United States Patent
Oliver et al.

(10) Patent No.: US 7,858,107 B2
(45) Date of Patent: Dec. 28, 2010

(54) FLEXIBLE BIORESORBABLE HEMOSTATIC PACKING AND STENT HAVING A PRESELECTABLE IN-VIVO RESIDENCE TIME

(75) Inventors: Dana A. Oliver, Jacksonville, FL (US); Matthew J. Halvorsen, Hopkinton, NH (US); Leah Kavanagh, Jacksonville, FL (US)

(73) Assignee: Medtronic Xomed, Inc., Minneapolis, MN (US)

( * ) Notice: Subject to any disclaimer, the term of this patent is extended or adjusted under 35 U.S.C. 154(b) by 1361 days.

(21) Appl. No.: 10/938,999

(22) Filed: Sep. 10, 2004

(65) Prior Publication Data

US 2006/0057182 A1 Mar. 16, 2006

(51) Int. Cl.
*A61K 31/728* (2006.01)
*A61F 2/00* (2006.01)
(52) U.S. Cl. .......................... 424/423; 514/54
(58) Field of Classification Search ........................ None
See application file for complete search history.

(56) References Cited

U.S. PATENT DOCUMENTS

| 4,140,537 | A | * | 2/1979 | Luck et al. ............... 106/160.1 |
| 4,280,954 | A | | 7/1981 | Yannas et al. ............ 260/123.7 |
| 4,851,521 | A | | 7/1989 | Della Valle et al. ......... 424/401 |
| 4,937,270 | A | | 6/1990 | Hamilton et al. ............ 514/777 |
| 4,957,744 | A | | 9/1990 | Della Valle et al. ......... 424/401 |
| 5,017,229 | A | | 5/1991 | Burns et al. ................. 106/162 |
| 5,527,893 | A | | 6/1996 | Burns et al. .................... 514/53 |
| 5,658,582 | A | | 8/1997 | Dorigatti et al. ............. 424/402 |
| 5,824,335 | A | | 10/1998 | Dorigatti et al. ............. 424/443 |
| 6,294,202 | B1 | | 9/2001 | Burns et al. ................. 424/488 |
| 6,458,889 | B1 | * | 10/2002 | Trollsas et al. ............. 525/54.1 |
| 6,632,802 | B2 | | 10/2003 | Bellini et al. ................. 514/54 |
| 6,723,709 | B1 | | 4/2004 | Pressato et al. ............... 514/54 |
| 2003/0187381 | A1 | | 10/2003 | Greenawalt et al. ........... 604/11 |
| 2006/0057182 | A1 | * | 3/2006 | Oliver et al. ................ 424/423 |

FOREIGN PATENT DOCUMENTS

GB 2151244 7/1985

* cited by examiner

*Primary Examiner*—Shanon A Foley
(74) *Attorney, Agent, or Firm*—Dicke, Billig & Czaja, PLLC

(57) ABSTRACT

The invention provides a flexible bioresorbable foam having hemostatic properties and a preselectable in-vivo residence time. The foam includes a blend of collagen and a hyaluronic acid component such as hyaluronic acid or a derivative thereof, typically, the hyaluronic acid component is present in a range of from about 70 to about 90 percent.

29 Claims, No Drawings

FLEXIBLE BIORESORBABLE HEMOSTATIC PACKING AND STENT HAVING A PRESELECTABLE IN-VIVO RESIDENCE TIME

FIELD OF THE INVENTION

The present invention relates generally to the field of bioresorbable packing and stents, and more specifically to a flexible bioresorbable foam, useful for post-operative or drug delivery use, having both hemostatic properties and a preselectable in-vivo residence time.

BACKGROUND OF THE INVENTION

Various types of sterile packing and stents are used in the medical and surgical fields for keeping tissues apart or preventing adhesion. Such uses include, but are not limited to, nasal packing and sinus stents, packing for inner ear surgery, tympanoplasty, exostosis, orbital decompression, as well as various orifice restenosis prevention uses. Personal uses such as tampons, bandaging and the like also involve sterile packing materials.

Such packing and stents have been made from gauzes, microfibers, nonfibrous expandable packing, such as tampons, and the like. These types of packing are not bioresorbable and can cause injury or discomfort upon removal, as well as causing toxic shock syndrome if left internally for more than a day or two.

In an attempt to prevent such reactions, while continuing to prevent adhesion and tissue necrosis, resorbable packing and stent devices have been developed. Such packing materials have typically included hyaluronic acid (HA), or salts of hyaluronic acids, which are naturally occurring mucopolysaccharides found in various body fluids and connective tissues. Thus, HA is biocompatible. It has been adapted for use as a surgical aid to prevent tissue contact and adhesion formation. However, HA has a very high solubility, and thus poor liquid absorption, and tends to quickly disperse when exposed to such liquids. This reduces HA materials' effectiveness in areas such as surgical wounds which exude blood and other fluids. Crosslinking has created somewhat insoluble HA materials. Further, other biocompatible materials such as polysaccharides, especially methylcellulosic materials have been combined with the hyaluronic acid to produce packing materials which are resorbable but are also insoluble and have a longer in-vivo residence time before they dissolve into gels and are absorbed by the body tissues. These materials also have increased fluid absorption capabilities. Such materials stop bleeding only by effect of compression and packing and do not have any inherent hemostatic properties.

Collagen is also known for use in the medical field; it is a major protein constituent of connective tissue and is widely used in medical and surgical applications such as sutures, grafts and surgical prostheses. Typical sources include calfskin, bovine Achilles tendons, cattle bones, porcine tissue, human cadaver tissue, and rat tails. Collagen, as an animal protein, is bioresorbable, even when crosslinked to reasonable levels. Collagen is available in a variety of forms including powders and fibrils, and in aqueous solution. Collagen may be provided in insoluble or soluble forms.

It has now been discovered that a flexible bioresorbable foam for packing, post-operative use, and other medical uses may be created having both hemostatic properties and a variable preselectable resorption time (also known as an in-vivo residence time). The foam is formed from a blend of collagen and hyaluronic acid or derivative thereof.

SUMMARY OF THE INVENTION

An embodiment of the invention provides a flexible bioresorbable foam having both hemostatic properties and a variable preselectable resorption time.

More specifically, an embodiment of the invention provides a flexible bioresorbable foam having hemostatic properties and a variable preselectable in-vivo residence time or resorption time, comprising a blend of collagen and a hyaluronic acid component, which may be hyaluronic acid or a derivative thereof.

One embodiment of the invention provides a flexible bioresorbable foam having hemostatic properties and a variable preselectable resorption time comprising a blend of collagen and an esterified hyaluronic acid.

Another embodiment of the invention includes a flexible bioresorbable foam wherein the blend includes from about 70 to about 90 percent by weight of hyaluronic acid component.

An embodiment of the invention also provides a medical device wherein said device is a stent intended for insertion between two tissue surfaces of a patient to control bleeding and prevent adhesion. The medical device can be a stent intended for insertion into body cavities and/or orifices such as the eye, ear, nose, throat, anal or vaginal orifices and the like.

Another embodiment of the invention also provides a drug delivery and release device for implantation within the body comprising a drug and a flexible bioresorbable foam having hemostatic properties and a variable preselectable resorption time comprising collagen and hyaluronic acid or a derivative thereof.

A further embodiment of the invention, is a medical device comprising a flexible bioresorbable foam having hemostatic properties and a preselectable in-vivo residence time comprising a blend of collagen and an esterified hyaluronic acid.

Another embodiment of the invention provides a method of making flexible bioresorbable foam having hemostatic properties and a variable preselectable resorption time comprising the steps of:

a) providing a blend of collagen and an hyaluronic acid component comprising from about 70 to about 90 weight percent of said esterified hyaluronic acid, b) mixing with water to form a suspension;

c) freezing and lyophilizing the blend at 0° C. or below;

d) crosslinking to form a flexible crosslinked product, and, e) sterilizing and performing chain scission on said crosslinked product by means of bombardment with gamma rays or electrons.

In one method of making the bioresorbable flexible foam of an embodiment of the invention, the foam is crosslinked using a chemical crosslinking agent.

These terms when used herein have the following meanings.

1. The term "bioresorbable" as used herein, means capable of being absorbed by the body.

2. The term "hemostat" means a device or material which stops blood flow.

3. The term "stent" means a material or device used for separating tissue and holding it in such separated position.

4. The term "lyophilizing" means freeze-drying.

5. The term "resorption time" and "in-vivo residence time" are used interchangeably, and refer to the time between insertion into the body and the time at which the material has been substantially absorbed into the tissues.

6. The term "adhesion" as used herein, refers to the sticking together of tissues which are in intimate contact for extended periods.

7. The term "preselectable in-vivo residence time" means that foams of the invention may be formed that will have different in-vivo residence times to be useful for different applications.

DETAILED DESCRIPTION OF THE PREFERRED EMBODIMENTS

The following detailed description describes certain embodiments and is not to be taken in a limiting sense. The scope of the present invention is defined by the appended claims.

The bioresorbable hemostatic packing provided herein may be used in any manner in which sterile packing and/or stents are normally used in the surgical or medical fields, including uses for which control of low volume bleeding and adhesion prevention are important. Such uses include, but are not limited to, nasal packing and sinus stents, packing for inner ear surgery, tympanoplasty, exostosis, orbital decompression, as well as various orifice restenosis prevention uses. The packing materials may also be used as single or combination drug delivery systems for humans or mammals.

Bioresorbable foams of an embodiment of the invention are formed from a blend of a hyaluronic acid component and collagen. Varying ratios of the components may be used in the blends according to the application desired, e.g., 50/50, 60/40 etc. A typical blend may comprise from about 70 to about 90 weight percent of the hyaluronic acid component, and correspondingly from about 10 to about 30 weight percent of collagen. In one embodiment, the blend contains from about 70 to about 80 weight percent of the hyaluronic acid or derivative thereof. The ratios of such blends can be selected by the particular application anticipated. For example, higher amounts of collagen will increase the hemostatic effect somewhat.

Collagen materials useful in blends of an embodiment of the invention are absorbable collagen materials from any source, e.g., corium collagen, tendon collagen, and the like, available commercially from such companies as Datascope® and Fibrogen, Inc. In one embodiment, the blends are formed of a microfibrillar collagen foam that includes a collagen flour. Such collagen materials are available from Davol Inc., a subsidiary of C. R. Bard, Inc., as Avitene®.

Useful hyaluronic acid components include hyaluronic acid, derivatives thereof, and mixtures thereof. One particularly useful derivative is esterified hyaluronic acid. Useful ester derivatives may be partial or total esters of hyaluronic acid; e.g., hyaluronic acid esterified with aliphatic or araliphatic esters such as ethyl esters, octadecyl esters, benzyl esters and mixtures thereof. In one embodiment the blend comprises a partial esterified hyaluronic acid; especially, an esterified HA having an esterification of at least about 60%. One useful esterified hyaluronic acid has an esterification level of from about 60% to about 70%. Such materials are available commercially from Fidia Advanced Biopolymers, S.r.l. under the trade name Hyaff®.

The in-vivo residence times of flexible foams of an embodiment of the invention may be selected to be from about 5 days to about 28 days; in some embodiments, the foam will have an in-vivo residence time of from about 5 days to about 14 days. The in-vivo residence time for the flexible bioresorbable foams of an embodiment of the invention is controlled by adjusting the re-suspension shear parameters, the level of crosslinking of the foam ingredients to produce the desired level; the sterilization bombardment must also be controlled in order to control the chain scission caused by such bombardment.

In one embodiment, the foams are formed by a method which includes the formation of a suspension of the collagen and the esterified hyaluronic acid in water. The suspension is formed by mixing with conventional mixers until suspended. The suspension is mixed at a shear rate of from about 0.25 minutes/liter to about 3.0 mins./liter, and at a speed of from about 7,000 rpm to about 10,000 rpm. The suspension is then metered into lyophilization trays with a series of cavities. Typical trays have cavities nominally about 4 cm by 1.3 cm by 1 cm. The suspended solution is then freeze-dried into solid foam blocks using well known procedure involving vacuum conditions at temperatures which are less than the freezing temperature of water, i.e., less than 0° C. After 0° C. is reached, the temperature is then reduced further over time, and cycled; e.g., the temperature is reduced by a few degrees then maintained at the lower temperature for a period of time, and then reduced again. Finally, the temperature reaches a low of about $-45°$ C. where it is maintained for the period required to complete the lyophilization, e.g., at least about 10 hours, and perhaps as much as 24-30 hours. The drying portion of the lyophilization is performed at a vacuum set point of about 75 mm of mercury (Hg) with the temperature being raised to about 0° C. and maintained there for at least about 2 hours, and up to about 6 hours, then raised to at least about 25° C. to a period of from about 4 hours to about 40 hours.

Upon completion of lyophilization, the foam is then ready to be crosslinked. Crosslinking may be accomplished by dehydrothermal crosslinking, or by exposure to a chemical crosslinking agent. In dehydrothermal crosslinking, the foam is dehydrated to reduce the moisture content to the temperature at which crosslinking occurs, typically to less than about 1%. The product is subjected to elevated temperatures and/or vacuum conditions until crosslinking occurs. Useful combinations of such conditions include vacuum of at least about $10^{-5}$ mm of mercury, and temperatures of at least about 35° C. Naturally, if vacuum is not used, much higher temperatures are required, e.g., above 75° C. The conditions are maintained for at least about 10 hours, typically for about 24 hours until the desired molecular weight has been achieved.

If chemical crosslinking is desired, useful chemical crosslinking agents include aldehydes, e.g., formaldehyde vapor, which can be used by pumping it into a room containing the lyophilized foam and allowed to contact the foam for at least about 2 hours, preferably at least about 5 hours. After the desired exposure time is complete, the crosslinking agent is evacuated from the room.

After crosslinking, the foam is then ready for compression, packaging and sterilization, typically by bombardment with gamma rays or electron beam bombardment. The bombardment both kills bacteria and performs chain scission on the foam. It is important that the sterilization/chain scission procedure and the crosslinking procedure be balanced to produce the desired crosslinking level to achieve the in-vivo residence time desired. The bioresorbable foam of the invention is flexible and does not require any rehydration.

The bioresorbable foam of the invention can be easily handled either wet or dry and may be squeezed, and/or cut to required size. The foam will contour to the body cavity or wound as required, and provides chemical hemostasis as well as preventing adhesion, and minimizing swelling and edema.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, bio-medical, and biomaterials arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A flexible bioresorbable foam having hemostatic properties and a preselectable in-vivo residence time wherein the flexible bioresorbable foam consists of crosslinked collagen blended with a hyaluronic acid component.

2. A flexible bioresorbable foam according to claim 1 wherein said blend comprises from about 70 to about 90 percent by weight of said hyaluronic acid component.

3. A flexible bioresorbable foam according to claim 2 wherein said blend comprises from about 70 to about 85 percent by weight of said hyaluronic acid component.

4. A flexible bioresorbable foam according to claim 1 wherein said hyaluronic acid component is selected from the group consisting of hyaluronic acid, esterified hyaluronic acid, and mixtures thereof.

5. A flexible bioresorbable foam according to claim 4 wherein said hyaluronic acid component is esterified hyaluronic acid or a mixture of esterified hyaluronic acid and hyaluronic acid.

6. A flexible bioresorbable foam according to claim 5 wherein said esterified hyaluronic acid has an esterification level of from about 60 percent to about 70 percent.

7. A flexible bioresorbable foam according to claim 5 wherein said esterified hyaluronic acid is selected from the group consisting of a benzyl ester of hyaluronic acid, an ethyl ester of hyaluronic acid and mixtures thereof.

8. A flexible bioresorbable foam according to claim 1 wherein said crosslinked collagen is a microfibrillar collagen.

9. A flexible bioresorbable foam according to claim 1 wherein said preselectable residence time ranges from about 5 days to about 28 days.

10. A flexible bioresorbable foam according to claim 9 having a preselectable in-vivo residence time of from about 5 days to about 14 days.

11. A flexible bioresorbable foam according to claim 1 wherein a suspension is formed from said blend at a shear rate of from about 0.25 minutes/liter to about 3.0 mins./liter, and from about 7,000 rpm to about 10,000 rpm.

12. A flexible bioresorbable foam according to claim 1 wherein said foam is crosslinked by means of a method selected from dehydrothermal crosslinking and chemical crosslinking.

13. A flexible bioresorbable foam according to claim 12 using a chemical crosslinking agent.

14. A flexible bioresorbable foam according to claim 13 wherein said chemical crosslinking agent is formaldehyde vapor.

15. A flexible bioresorbable foam according to claim 1 wherein said foam is sterilized and molecular chain scission is performed by bombardment with gamma rays or a beam of electrons.

16. A medical device comprising a flexible bioresorbable foam having hemostatic properties and a preselectable in-vivo residence time wherein the flexible bioresorbable foam consists of crosslinked collagen blended with a hyaluronic acid component.

17. A medical device according to claim 16 wherein said blend comprises from about 70 to about 90 percent by weight of said hyaluronic acid component.

18. A medical device according to claim 16 wherein said hyaluronic acid component is selected from the group consisting of hyaluronic acid, esterified hyaluronic acid, and mixtures thereof.

19. A medical device according to claim 18 wherein said hyaluronic acid component is esterified hyaluronic acid or a mixture of esterified hyaluronic acid and hyaluronic acid.

20. A medical device according to claim 19 wherein said esterified hyaluronic acid has an esterification level of from about 60 percent to about 70 percent.

21. A medical device according to claim 19 wherein said esterified hyaluronic acid is selected from the group consisting of a benzyl ester of hyaluronic acid, an ethyl ester of hyaluronic acid, and mixtures thereof.

22. A medical device according to claim 16 wherein said crosslinked collagen is a microfibrillar collagen.

23. A medical device according to claim 16 wherein said variable residence time ranges from about 5 days to about 28 days.

24. A medical device according to claim 16 wherein said device is a stent intended for insertion into a cavity or orifice of the body or to separate opposing tissue surfaces of a patient to control bleeding and prevent adhesion.

25. A medical device according to claim 24 wherein said stent is intended for insertion into the cranial cavity, the thoracic cavity, the abdominal cavity or the pelvic cavity.

26. A medical device according to claim 25 wherein said stent is intended for insertion into the eye, ear, nose or throat.

27. A drug delivery device for implantation within the body comprising a drug and the flexible bioresorbable foam of claim 1.

28. A drug delivery device according to claim 27 wherein said foam comprises a blend of from about 70 to about 90 percent by weight of a hyaluronic acid component and correspondingly, from about 10 to about 30 percent by weight of collagen.

29. A drug delivery device according to claim 28 wherein said hyaluronic acid component is selected from the group consisting of hyaluronic acid, esterified hyaluronic acid and mixtures thereof.

* * * * *